United States Patent [19]
Tröster et al.

[11] Patent Number: 6,084,237
[45] Date of Patent: Jul. 4, 2000

[54] METHOD AND APPARATUS FOR THE ANALYTICAL DETERMINATION OF TRACES

[75] Inventors: Klaus Tröster, Augsburg; Antonius Kettrup, Arnsberg, both of Germany

[73] Assignee: GSF-Forschungszentrum für Umwelfund Gesundheit GmbH, Oberschleissheim, Germany

[21] Appl. No.: 09/131,465

[22] Filed: Aug. 10, 1998

[30] Foreign Application Priority Data

Aug. 11, 1997 [DE] Germany ............ 197 34 460

[51] Int. Cl.$^7$ ........................ H01J 49/10
[52] U.S. Cl. ........................ 250/288
[58] Field of Search ............ 250/288, 281, 250/282

[56] References Cited

U.S. PATENT DOCUMENTS 5,663,561  9/1997  Franzen et al. .............. 250/288

Primary Examiner—Kiet T. Nguyen
Attorney, Agent, or Firm—Klaus J. Bach

[57] ABSTRACT

In a method and apparatus for the analytical determination of trace compounds, portions of a sample disposed on a sample carrier are irradiated with light having an energy density of 1 to 100 MW/cm$^2$ so that any organic trace compounds are removed from the irradiated sample portions, the removed trace compounds are collected by a capillary which is adjustably supported so as to be movable in close proximity to the irradiated sample portion and the organic trace compounds collected by the capillary are supplied to an analysis apparatus for detection.

11 Claims, 3 Drawing Sheets

METHOD AND APPARATUS FOR THE ANALYTICAL DETERMINATION OF TRACES

BACKGROUND OF THE INVENTION

The invention relates to a method and apparatus for the analytical determination of traces.

In M. J. Cohen et al Journal of Chromatographic Science, 1970, 8, 330–337, an ion drift spectrometer (IMS) possibly coupled with a mass spectrometer is disclosed for use in a sensitive analysis method for certain organic compounds. It is also known from Baum, M. A., Etherton, R. L.; Hill, H. H. Jr; Anal. Chem. 1983, 55; 1761–1766, to use an IMS apparatus as a detector for a gas chromatograph (GC) wherein the capillary of the GC apparatus was connected to the IMS apparatus.

Since with conventional IMS apparatus, no care has been taken to keep the volume and the reverse mixing of the sample chamber at a minimum, it is necessary with present apparatus to use substantially larger amounts of a substance as it would be necessary with substantially smaller probe chambers or with a capillary and a relatively long waiting time is needed for the substance to be again flushed out of the apparatus so that a new sample can be tested.

An analysis indicating the location of the traces cannot be obtained with any of the apparatus.

It is the object of the present invention to provide a method and apparatus for a trace analysis by which also the location of the traces can be determined.

SUMMARY OF THE INVENTION

In a method and apparatus for the analytical determination of trace compounds, portions of a sample disposed on a sample carrier are irradiated with light having an energy density of 1 to 100 $MW/cm^2$ so that any organic trace compounds are removed from the irradiated sample portions, the removed trace compounds are collected by a capillary which is adjustably supported so as to be movable in close proximity to the irradiated sample portion and the organic trace compounds collected by the capillary are supplied to an analysis apparatus for detection.

If the conventional sample chamber of an IMS apparatus which has a volume of about 10 ml is replaced by a smaller chamber of about 3.5 ml or by a 0.5 m long quartz capillary with about 0.1 ml volume, the sample volume is substantially reduced which leads to a substantially smaller dilution and reverse mixing of the sample. "Reverse mixing" refers to mixing of volume elements in flow direction which is physically in its effects similar to diffusion. Since, as a result of the smaller reaction chamber, the substance volume to be analyzed is supplied to the ion molecule reactor in a substantially shorter period of time, the detection limit is lowered and the signals obtained are substantially narrower and higher. If instead of the relatively voluminous sample chamber used in connection with present apparatus a capillary is used the volume of the inlet system and the dilution as well as the reverse mixing of the substances to be analyzed are substantially reduced. In this way, narrow signals and small detection limits are obtained. It is however to be noted that possible adsorption of the substances being transported by the inner surface of the transport means may also lead to a kind of reverse mixing and should therefore be minimized.

Since with the experimental detection methods, the substance volume which is disposed in the capillary could only be roughly estimated the increase of the sensitivity could not be accurately determined. However, in an apparatus using capillaries, the sensitivity is increased at least 10 to 100 fold.

Another advantage resides in the fact that the IMS apparatus can be miniaturized. The capillary also represents a sensitive "nose" for the surveillance of air with regard to noxious compounds. With multipoint measurements, it is possible with the use of capillaries to increase the interrogation rate.

Below, an embodiment of the invention will be described on the basis of the accompanying drawings.

DESCRIPTION OF A PREFERRED EMBODIMENT

Figure 1B:
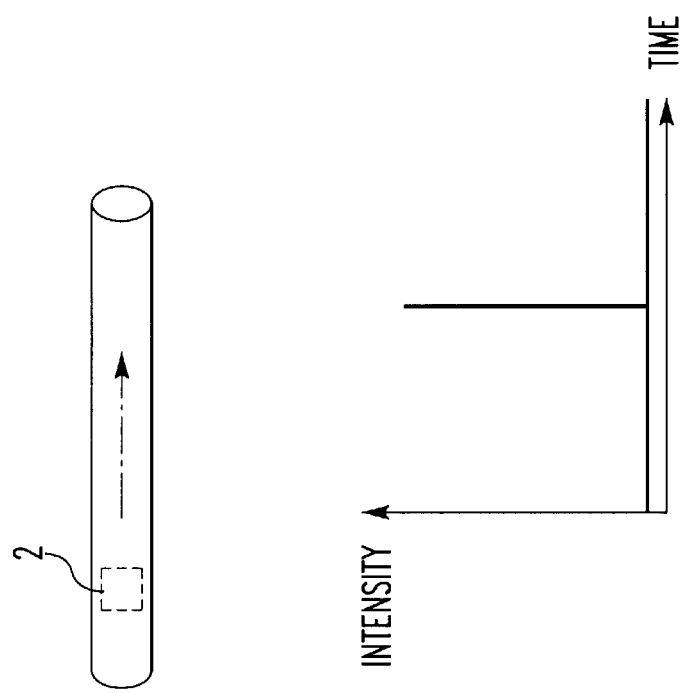
FIG. 1B shows a transport line without increased volume and the time-dependent signal generated therewith.
Figure 1A:
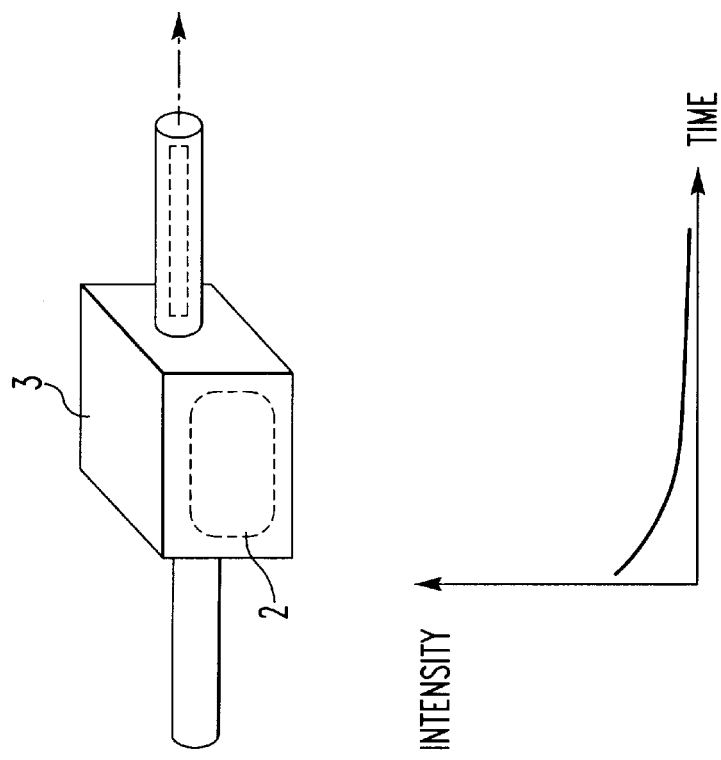
FIG. 1A shows a transport line arrangement with an increased volume and the time-dependent signal generated therewith.

FIG. 1A shows the influence of the transport volume on the detector signal depending on time. On top, a transport line with an increased volume 3 into which a gas sample 2 is introduced for measuring purposes is shown. Below, the detector signal obtained by the arrangement is shown.

FIG. 1B shows on top an arrangement without an increased measuring volume. Below the detector signal obtained by the arrangement is shown.

If a large transport volume 3 is used which permits a fast and almost complete reverse mixing the gas sample 2 introduced at a certain point in time is diluted. As a result, the detector signal over time starts at a relatively low value and then falls further with increasing dilution of the sample.

If no increased volume is provided in the transport line as shown in FIG. 1B, the detector shows no response until the sample passes by the detector, but then the detector signal shows a sharp peak. In this way, the detection limit is substantially reduced, that is, even small samples or small traces can be recognized.

Figure 2:
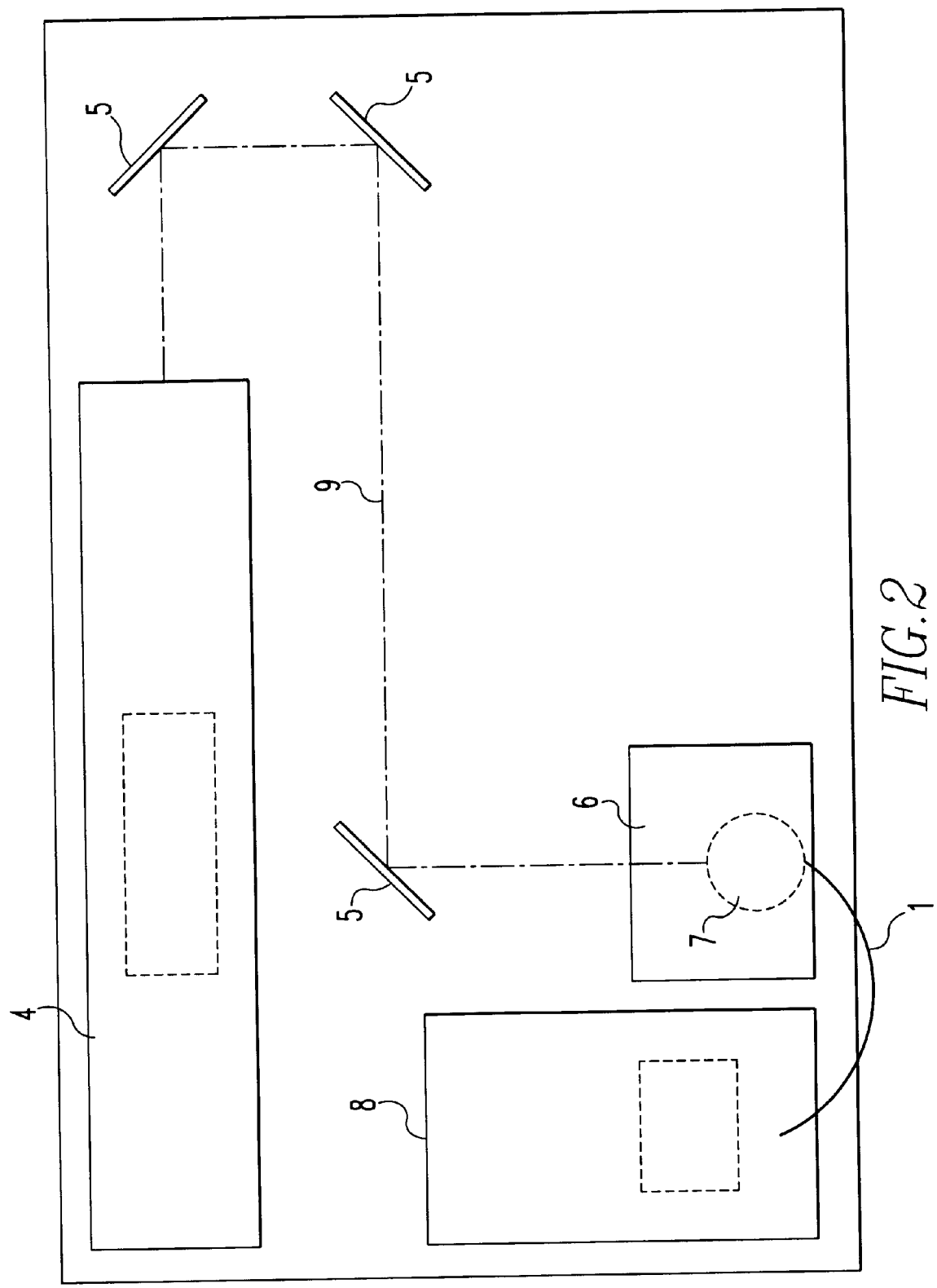
FIG. 2 shows schematically an apparatus for determining traces.

In the detecting arrangement as shown in FIG. 2, a laser is used as the light source 4. The laser beam 9 is coupled, by way of mirrors 5, into a microscope 6 and focused onto a sample 11 (not shown in FIG. 2, but in FIG. 3). The sample 11 is disposed in a desorption chamber 7. The described gas sample 2 is conducted to the measuring apparatus 8 by way of a capillary 1.

Figure 3:
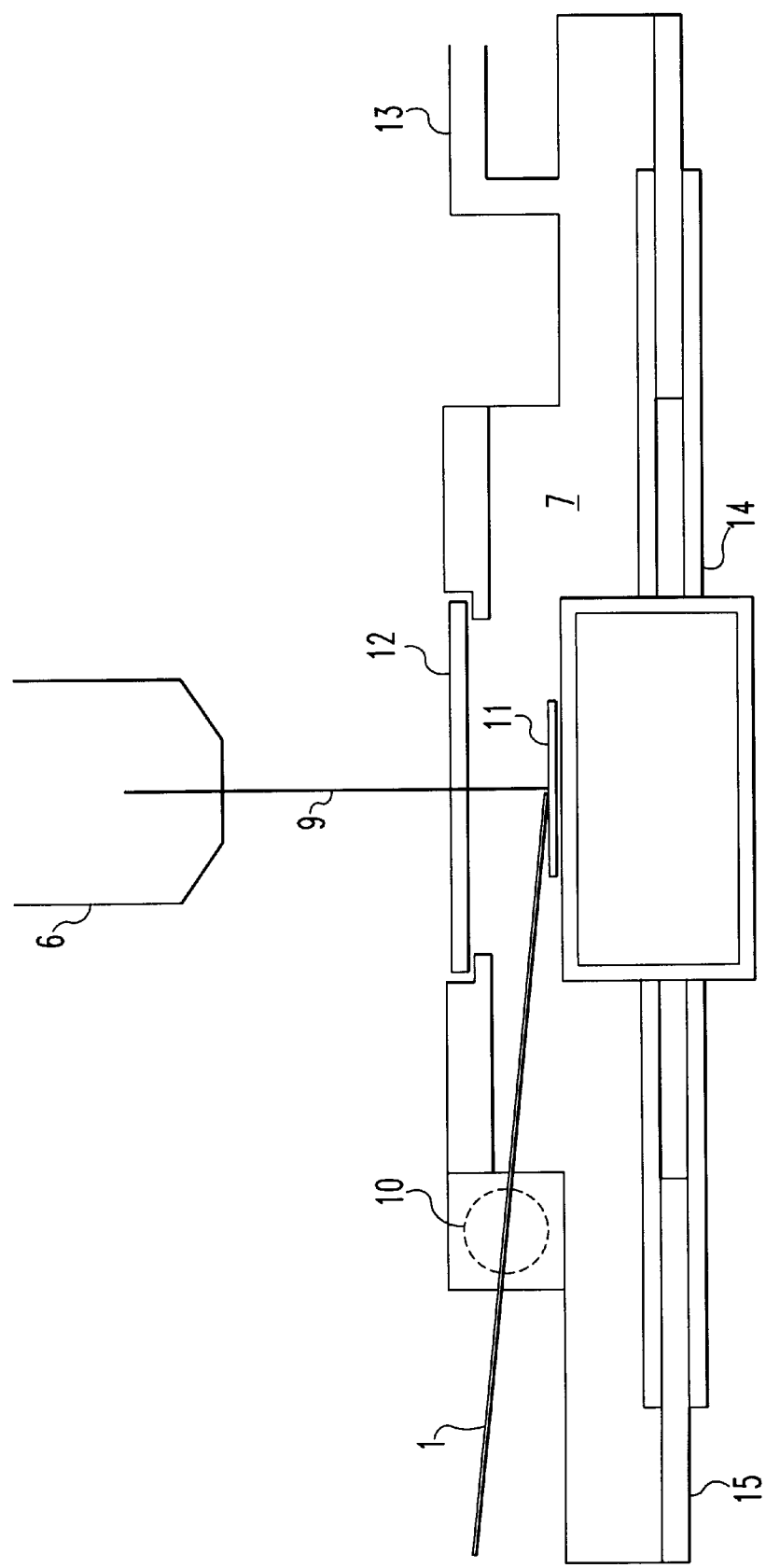
FIG. 3 shows a laser desorption unit.

For a location-dependent analysis of organic substances by means of an ion drift spectrometer, it is helpful to utilize a laser desorption chamber which shields the sample to be measured from the laboratory air since otherwise the measuring result can be adversely affected by contamination contained in the laboratory air. For this purpose, the desorption chamber 7 as shown in FIG. 3 is provided. In order to avoid any contamination of the inert gas atmosphere by organic compounds no organic lubricants or sealing materials such as silicones or rubber are used in the design of the laser desorption chamber. Inspite of this, the sample can be positioned in the laser desorption chamber in any desired inert gas atmosphere under a microscope lens system in such a way that the organic compounds can be desorbed by a laser beam at room temperature on a surface area of about 50 $\mu m^2$. Also, the molecules released thereby can be removed from the laser desorption chamber 7 by way of a capillary 1 and can be supplied to an analysis apparatus such as an IMS apparatus.

The laser beam 9 emerges from the microscope 6 at the bottom and passes through the window 12 and reaches the sample 11. The capillary 1 extends through a capillary penetration 10 and reaches up to a close vicinity of the desorption location. The capillary penetration consists of a ball of insulating material with a central bore in which the capillary is snugly received. The ball is sealed in the desorption chamber 7 by spherical grinding and a metal ring or Teflon ring in such a way that the ball remains freely movable. The capillary 1 consists of glass or quartz. The capability of the capillary 1 to collect the desorption sample depends essentially on its distance from the desorption location. Consequently, the front opening of the capillary should be as close as possible to the desorption location without interfering with the laser beam. The capillary diameter should be larger than the laser spot on the sample. A size ratio 7 to 1 has been found to be advantageous. With excessively large size ratios (greater than 15), the detection sensitivity drops. If polarized substances are to be detected their adsorption in the capillary can be reduced by heating as well as by special deactivation materials such as silicon compounds. The heating of the capillaries is facilitated if the glass capillary is surrounded by a metal tube or by the use of a metal capillary which has a quartz-coated inner surface. In both cases, the metal layer is resistance-heated. The electric power connections are not shown in the drawings.

The laser desorption chamber 7 is disposed on a microscope table which is adjustable in an x, y and z direction. The movement of the microscope table in x and y direction is transferred to a sample carrier 14 of brass in whose center a sample holder (not shown) is arranged which can be removed downwardly. As a result, a sample can be accurately positioned on the sample holder with respect to the top part of the desorption chamber (of Al) and the lens of the microscope with an accuracy of 1 $\mu m$. The apparatus includes an aluminum cover which is bolted to a table by way of two retaining pins, a retaining plate and two legs. The microscope is also mounted on the table. As a result, the laser desorption chamber can be moved relative to the lens system only in z direction for adjusting the focus.

In order to seal the interior space of the desorption chamber 7 against laboratory air the movable sample carrier 14 is pressed by two annular plates against the annular carrier support structure 15 consisting of V2A. The lower annular plate of the sample carrier 14 is removable and so mounted that the play of the polished plates is 10 to 20 $\mu m$. Since lubricants could greatly affect the test results all tolerances must be so selected that appropriate slide properties can be achieved without the use of lubricants.

Also, the tolerance fitting between the removable sample holder of V2A and the brass carrier does not use any lubricants. In order to be able to examine samples of different thickness the height of the sample carrier is adjustable.

The laser beam coupled into the microscope enters the laser desorption chamber through a glass window and strikes the sample disposed on the sample carrier. With laser beam densities of 1–3 $MW/cm^2$ any organic compounds present are desorbed from the sample surface by the energy of the laser beam in a generally non-destructive fashion. The window 12 is mounted into the top part with rubber or silicon or similar seals only by means of brass retainers having a circumferential thread. In this way, the chamber is not fully gas tight but, by way of the gas inlet 13, a pressure of about 4 mbar can be generated in the laser desorption chamber with a gas flow of 400 ml/mm whereby the inflow of laboratory air into the laser desorption chamber is prevented. As a result, the laser desorption procedure can be performed independently of the laboratory air by flushing the interior of the chamber with any desirable gas. Furthermore, the internal pressure is sufficient to carry the laser-desorbed substances, mixed with the gas present in the chamber, in a volume flow of about 4 ml/min by way of a heated conduit to the IMS apparatus. Preferably, the flow through the capillary is as large, that is as fast, as possible. In this way, the time during which the gas sample 2 is in contact with the capillary is shortened. Also, the transport time for the sample through the capillary is reduced so that the subsequent location can sooner be irradiated and the desorption of the location can begin.

The following advantages are achieved:

IMS-spectra obtained by laser desorption with a location-resolution of about 50 $\mu m^2$ provide much better information than arrangements without laser desorption chamber.

The measurements are not falsified by lubricants in the laser desorption chamber.

The measurements are not affected by the formation of gases from sealing materials such as rubber or silicones.

The measurements are not affected by any laboratory air present at the desorption location.

With the pressure difference between the laser desorption chamber and the IMS apparatus the desorbed substance can be forced into the IMS apparatus which, because of the not sealtight drift cell of the IMS apparatus, results in fewer contaminations in the IMS spectrum than could be obtained with suctioning at the gas outlet of the IMS apparatus.

With the pressure difference between the laser desorption chamber and the IMS apparatus, the desorbed substance can be supplied under pressure to any measuring apparatus if this is advantageous.

Laser desorption is possible in any gas for example an inert gas such as nitrogen or helium.

The internal pressure and the volume flow to the IMS apparatus through the heated conduit are adjustable by control of the flow.

A minimal distance between the lens system and the sample holder is 6.8 mm which is sufficient for a lens system with large operating distance and 1000 fold enlargement.

A combination of the location resolution by the laser desorption at room temperature and transport of the desorbed molecules at higher temperature which is needed for a high detection sensitivity becomes possible with the laser desorption chamber.

It is advantageous if an ion drift spectrometer (IMS) or ion drift spectrometers with subsequent mass spectrographs (IMS/MS) as detectors are coupled with a unit which desorbs by laser with good location resolution and supplies the desorbed substances to an analysis apparatus.

Laser desorption without location resolution has the following disadvantages:

The location resolution obtained by the selection of a particular area is in the square millimeter to square centimeter range and consequently, is quite inadequate. Furthermore, such a method cannot detect contamination on an organic matrix such as plastic material since the gas volume generated by a plastic material, resin, cement etc. is so large that the contamination signal itself is no longer detectable.

With the method and apparatus according to the invention a laser beam is applied to the surface to be analyzed which desorbs all the organic compounds in a surface area of about 50 $\mu m^2$. The molecules released in this way are carried by a carrier gas to the IMS apparatus which is a sensitive detector for certain organic substances and are detected thereby. It is possible to determine the composition at various parts of a surface to obtain an indication concerning the reason for the difference. In this way, it is for example possible to find explanations for the failure of electronic components (wafers). As a result, the manufacturing process can be optimized.

To show the operability of the complete apparatus p-methoxylbenzoin acid was desorbed by an argon ion laser at $\lambda$=488 nm with a laser power density of 2–3 MW/cm$^3$. The neutral molecules vaporized in the process were captured by a transport means, in this case a heated capillary, and supplied to the IMS apparatus where the molecules were detected upon arrival. During the laser desorption, and for some minutes thereafter, an IMS spectrum was taken every seven seconds in order to determine the time-dependent signal intensity of the molecules arriving in the IMS apparatus. By measurements of p-methoxybenzoin acid with an IMS/MS apparatus, the signal with $K_0$=1.76 cm$^2$/(VS) observed during laser desorption could be clearly determined to be the reason for the IMS signal of the protonized molecule ion (MH) of p-methoxylbenzoinacid, which proves that this substance is not destroyed during the laser desorption procedure.

A location resolution in the $\mu m^2$ range can be obtained therewith.

The substances can be desorbed directly from the sample surface and supplied to the analysis apparatus without the use of a solvent as an extraction means. Solid samples can be measured without expensive preparation whereby the sampling speed can be substantially increased and costs can be reduced. For most carrier materials such as silicon wafers or metals the method is non-destructive.

The matrix in which the substance to be analyzed is disposed can be masked out to a large degree so that only suspicious areas are irradiated by the laser whereas the surrounding areas remain cold.

Many ways are known to transfer solid, liquid or gaseous samples into the separation column of a gas chromatograph. With surface examinations, a certain location resolution has been achieved in that material from certain selected areas was scraped off and extracted by a solvent and injected into the column, or the solvent was applied for extraction directly to predetermined surface areas and the extraction solution was then injected into a gas chromatograph. The location resolution obtainable with such methods is in the square millimeter to square centimeter range and is consequently relatively bad. Also, the procedure is dependent on how well the substances can be extracted with the solvents utilized.

With the combination of location resolution, laser desorption and GC in accordance with the present invention, a laser beam is effective on the surface to be analyzed which desorbs all the organic compounds on a surface area of about 10–100 $\mu m^2$. The molecules released in this way are collected by a heated capillary which is placed closely adjacent the surface area being desorbed and are transported to the analysis apparatus.

This provides for the following advantages:

A location resolution in the $\mu m^2$ range is obtained. The substances can be desorbed directly from the sample surface and supplied to the analysis apparatus without the use of a solvent as an extraction means.

The laser desorption is substantially faster than the extraction by a solvent which increases sampling speed and reduces costs. The matrix in which the substance to be analyzed is disposed can be masked out so that only suspicious locations are exposed to the laser beam whereas the surrounding matrix remains cold. Since the laser desorption will rarely lead to a fragmentation of organic molecules the libraries already present can still be used for the identification of a substance.

Since the gas chromatograph technology (GC) is at a substantially higher state of development and is more widely used than ion drift spectrometers, a gas chromatograph (GC) is generally more suitable for commercial use.

However, newest developments show that gas chromatographs (GC) have lower detection limits than ion drift spectrometers (IMS) and are therefore more suitable for use as highly sensitive detectors.

What is claimed is:

1. A method for the analytical determination of traces comprising the following steps:

a) irradiating a portion of a sample surface with light for the removal of trace organic compounds to be detected wherein the light energy density is between 1 and 100 MW/cm$^2$, b) collecting the removed organic compounds with a capillary wherein the capillary has a diameter of at least three times that of the irradiated portion, and c) supplying the organic trace compounds in a carrier gas flow to an analysis apparatus and determining the trace compounds in the analysis apparatus.

2. A method according to claim 1, wherein, as capillary, a heated capillary is used.

3. A method according to claim 1, wherein said capillary is deactivated at its inner surface.

4. A method according to claim 1, wherein an ion drift spectrometer is used as analysis apparatus.

5. A method according to claim 1, wherein a gas chromatograph is used as analysis apparatus.

6. A method according to claim 1, wherein a mass spectrometer is used as an analysis apparatus.

7. An apparatus for the analytical determination of trace compounds, comprising:

a) a carrier for a sample whose surface is to be examined, b) a capillary so supported that its position relative to said sample on said sample carrier is adjustable, c) a light source for the irradiation of a sample on said sample carrier, said light source being adjustable relative to said sample and said capillary having a diameter three times as large as the diameter of the light spot generated on said sample by said light source for desorbing compounds desorbed from said sample, and d) an analysis apparatus for analysing said compounds.

8. An apparatus according to claim 7, wherein said capillary is heatable.

9. An apparatus according to claim 7, wherein the inner surface of said capillary comprises deactivated glass or quartz.

10. An apparatus according to claim 7, further comprising a desorption chamber consisting of:

a) a top part with a capillary penetration, a window and a gas inlet, and b) a bottom part which is movable relative to the top part.

11. An apparatus according to claim 10, wherein said bottom part is a sample carrier which is movable relative to the top part in a plane.

* * * * *